United States Patent
Jackson et al.

(10) Patent No.: US 10,500,201 B2
(45) Date of Patent: Dec. 10, 2019

(54) POROUS PARTICLES

(71) Applicant: LUCIDEON LIMITED, Penkhull, Stoke on Trent (GB)

(72) Inventors: Philip Robert Jackson, Stoke on Trent (GB); Mark Cresswell, Stoke on Trent (GB); Ian F. Campbell, Stoke on Trent (GB)

(73) Assignee: Lucideon Limited, Stoke-on-Trent (GB)

( * ) Notice: Subject to any disclaimer, the term of this patent is extended or adjusted under 35 U.S.C. 154(b) by 0 days.

(21) Appl. No.: 15/538,822

(22) PCT Filed: Dec. 21, 2015

(86) PCT No.: PCT/GB2015/054106
§ 371 (c)(1),
(2) Date: Jun. 22, 2017

(87) PCT Pub. No.: WO2016/102944
PCT Pub. Date: Jun. 30, 2016

(65) Prior Publication Data
US 2017/0348302 A1    Dec. 7, 2017

(30) Foreign Application Priority Data

Dec. 23, 2014  (GB) .................................. 1423148.4

(51) Int. Cl.
*A61K 31/485*    (2006.01)
*A61K 9/14*    (2006.01)
*C01B 33/154*    (2006.01)

(52) U.S. Cl.
CPC ............ *A61K 31/485* (2013.01); *A61K 9/143* (2013.01); *C01B 33/154* (2013.01)

(58) Field of Classification Search
None
See application file for complete search history.

(56) References Cited

U.S. PATENT DOCUMENTS

| | | | |
|---|---|---|---|
| 5,817,327 A | 10/1998 | Ducheyne et al. | |
| 2007/0196427 A1 | 8/2007 | Jokinen et al. | |
| 2007/0275068 A1* | 11/2007 | Martens ............... | A61K 9/1611 424/484 |

FOREIGN PATENT DOCUMENTS

| | | |
|---|---|---|
| EP | 1140027 A1 | 10/2001 |
| WO | WO2005/082781 A2 | 9/2005 |

(Continued)

OTHER PUBLICATIONS

NIDA Community Drug Alert Bulletin—Prescription Drugs, downloaded from https://archives.drugabuse.gov/PrescripAlert/, Jul. 28, 2017, 4 pages.

(Continued)

*Primary Examiner* — Robert A Wax
*Assistant Examiner* — Melissa S Mercier
(74) *Attorney, Agent, or Firm* — Barnes & Thornburg LLP (57) ABSTRACT

Processes for preparing porous particles are disclosed, in which the resulting particles release an encapsulated active ingredient more readily in aqueous media than they do in alcoholic media. Also described are the particles themselves, as well as tamperproof, abuse-deterrent, dosage forms comprising the porous particles. The release characteristics of the porous particles make them useful for overcoming drug-abuse techniques, such as dose-dumping in alcoholic media.

20 Claims, 10 Drawing Sheets

(56) References Cited

FOREIGN PATENT DOCUMENTS

WO     WO2015/035423 A2     3/2015
WO     WO2016/001670 A1     1/2016

OTHER PUBLICATIONS

Steven D. Passik et al., "Pain and Aberrant Drug-Related Behaviors in Medically Ill Patients With and Without Histories of Substance Abuse", Clin J Pain 2006; 22:173-181, pp. 173-181.
International Search Report and Written Opinion prepared for PCT/GB2015/054106, dated Mar. 3, 2016, 14 pages.
UK Search Report prepared for GB1423148.4, dated Sep. 30, 2015, 6 pages.
Czarnobaj, K. and Czarnobaj, J., "Sol-gel processed porous silica carriers for the controlled release of diclofenac diethylamine," J. Biomed. Mater. Res. B Appl. Biomater., 2008, 87, 114-120.
Maver, U. et al., "Novel hybrid silica xerogels for stabilization and controlled release of drug," International Journal of Pharmaceutics, 2007, 330, 164-174.

\* cited by examiner

POROUS PARTICLES

CROSS-REFERENCE TO RELATED APPLICATIONS

This application is a national stage entry under 35 USC § 371 of PCT International Application Number PCT/GB2015/054106, filed Dec. 21, 2015, which claims priority to United Kingdom Patent Application Number 1423148.4, filed Dec. 23, 2014, the entire disclosures of which are expressly incorporated by reference herein.

INTRODUCTION

The present invention relates to a process for preparing porous particles. More particularly, the invention relates to a process for preparing porous particles comprising an active ingredient. The present invention also relates to porous particles and solid dosage forms obtained by the described process.

BACKGROUND OF THE INVENTION

The abuse or misuse of medications represents an ongoing challenge for public health authorities. Whether intentional or accidental, the improper use of prescription medicaments has the potential to cause serious harm, ranging from reduced efficacy of the drug, to an increased expression of side effects and addictions.

Drug abusers have devised a variety of ways for achieving the "high" associated with improper substance use. A primitive, yet effective, technique sees a user crush or pulverize one or more oral dosages for subsequent administration via other routes, such as snorting, smoking or injecting. More elaborate methods involve extracting active ingredients from pharmaceuticals with the aid of household solvents or spirits like vodka, and even kitchen appliances, such as microwaves.

The threat to public health posed by improper drug use has prompted numerous public health authorities to task drug manufacturers with developing improved tamper-proof technologies. One approach has been to provide analgesic compositions comprising both agonistic and antagonistic ingredients, with the antagonistic effect designed to dominate when the composition is administered by an abusive route, such as by injection.

Other tamper-proof techniques have focused around so-called aversion technologies, which aim to discourage the would-be abuser by making the process more difficult and less pleasurable. Such approaches have involved using gelling agents to prevent a user from drawing the substance into a syringe, or including additives to cause increased burning and irritation in the nasal passages when snorted.

However, with abuse rates having quadrupled in the decade from 1990 to 2000[1,2], there remains a constant need for improved tamper-resistant technologies.

The present invention was devised with the foregoing in mind.

SUMMARY OF THE INVENTION

According to a first aspect of the present invention there is provided a process for the preparation of a plurality of porous particles comprising at least one active ingredient present within the pores, wherein the percentage release of the active ingredient from the pores of the particles into simulated intestinal fluid is greater than or equal to the percentage release of the active ingredient from the pores of the particles into 40% vol/vol ethanol in 0.1 M HCl, the process comprising the steps of:
  a) providing a mixture comprising water and HCl, said mixture having a pH of less than or equal to 2.5,
  b) adding to the mixture of step a) an inorganic porous particle monomer such that the molar ratio of water to the inorganic porous particle monomer is less than or equal to 12.5,
  c) adding to the mixture of step b) at least one active ingredient, wherein the at least one active ingredient comprises an opioid or opioid derivative,
  d) drying the mixture resulting from step c) at a temperature of greater than or equal to 60° C.,
  e) milling the material resulting from step d) to a particle size of 25-500 µm, and
  f) drying the resulting porous particles at a temperature of greater than or equal to 60° C.

According to a second aspect of the present invention there is provided a plurality of porous particles obtainable, obtained or directly obtained by a process defined herein.

According to a third aspect of the present invention there is provided a tamperproof or abuse-deterrent dosage form comprising a plurality of particles as defined herein.

According to a fourth aspect of the present invention there is provided a solid-dosage form comprising a plurality of particles as defined herein.

According to a fifth aspect of the present invention there is provided a particle comprising a porous substrate and at least one active ingredient present within the pores, wherein the at least one active ingredient is an opioid or opioid derivative and the particle has a particle size of 25-500 µm and a moisture content of less than or equal to 6% by weight, and wherein
  i. the percentage release of the at least one active ingredient from the particle in an aqueous solution of pH 6.8 at 37° C. is 30-50 after 1 hour, 45-65 after 2 hours, 60-80 after 4 hours and 85 or more after 10 hours, and
  ii. the percentage release of the at least one active ingredient from the particle in a solution of 40% vol/vol ethanol in 0.1 M HCl at 37° C. is 40 or less after 30 minutes, 50 or less after 1 hour and 65 or less after 2 hours.

According to a further aspect of the present invention there is provided a process for the preparation of a plurality of porous particles comprising at least one active ingredient present within the pores, the process comprising the steps of:
  a) providing a mixture comprising water and HCl, said mixture having a pH of less than or equal to 2.5,
  b) adding to the mixture of step a) an inorganic porous particle monomer such that the molar ratio of water to the inorganic porous particle monomer is less than or equal to 12.5,
  c) adding to the mixture of step b) at least one active ingredient,
  d) drying the mixture resulting from step c) at a temperature of greater than or equal to 60° C.,
  e) milling the material resulting from step d) to a particle size of 100-400 µm, and
  f) drying the resulting porous particles at a temperature of greater than or equal to 60° C.

According to a further aspect of the present invention there is provided a particle comprising a porous substrate and at least one active ingredient present within the pores, wherein the particle has a particle size of 100-400 µm and a moisture content of less than or equal to 6% by weight, and wherein i. the percentage release of the at least one active ingredient from the particle in an aqueous solution of pH 6.8 at 37° C. is 30-50 after 1 hour, 45-65 after 2 hours, 60-80 after 4 hours and 85 or more after 10 hours, and
ii. the percentage release of the at least one active ingredient from the particle in a solution of 40% vol/vol ethanol in HCl at 37° C. is 40 or less after 30 minutes, 50 or less after 1 hour and 65 or less after 2 hours.

DETAILED DESCRIPTION OF THE INVENTION

Processes of the Invention

As described hereinbefore, the present invention provides a process for the preparation of a plurality of porous particles comprising at least one active ingredient present within the pores, wherein the percentage release of the active ingredient from the pores of the particles into simulated intestinal fluid is greater than or equal to the percentage release of the active ingredient from the pores of the particles into 40% vol/vol ethanol in 0.1 M HCl, the process comprising the steps of:
 a) providing a mixture comprising water and HCl, said mixture having a pH of less than or equal to 2.5,
 b) adding to the mixture of step a) an inorganic porous particle monomer such that the molar ratio of water to the inorganic porous particle monomer is less than or equal to 12.5,
 c) adding to the mixture of step b) at least one active ingredient, wherein the at least one active ingredient comprises an opioid or opioid derivative,
 d) drying the mixture resulting from step c) at a temperature of greater than or equal to 60° C.,
 e) milling the material resulting from step d) to a particle size of 25-500 μm, and
 f) drying the resulting porous particles at a temperature of greater than or equal to 60° C.

It has surprisingly been found that particles prepared according to the above-described process present a number of advantages, most notably in the field of drug delivery. Until now, drug abusers have been endowed with a variety of methods for extracting active ingredients from prescription pharmaceuticals, which may then be concentrated to higher dosages for subsequent recreational use. Perhaps the most effective technique involves the use of one or more solvents to leach out the active ingredients from high-dosage controlled-release prescription medicaments. This so-called "dose-dumping" may also occur accidentally, whereby the simultaneous consumption of particular solvents, often ethanol present in alcoholic beverages, can induce the medicament to release its load almost instantaneously. Whether intentional or accidental, dose-dumping of this type can lead to abnormal quantities of the active ingredient in the blood steam, provoking a loss of efficacy, or an increased risk of side-effects and dependencies. The present invention now provides a novel means of significantly reducing the viability of such dose-dumping techniques by a means of accessing porous particles that release the active ingredient encapsulated therein at different rates in aqueous and alcoholic media. When compared with the release profile under physiological conditions, particles prepared according to the above-described process have been demonstrated to retard the release of the encapsulated active ingredient in alcoholic media, thus rendering the aforementioned dose-dumping techniques impractical, if not impossible. Particles prepared according to the above-described process therefore present a means of realising tamper-proof and abuse-deterrent medicaments. Furthermore, by varying the above-outlined processing parameters, the release profile of the resulting particles can be tailored according to a patient's needs. In addition to the above, the particles prepared according to the above-described method have been demonstrated to gradually (rather than immediately) release the encapsulated active ingredient under physiological conditions, at a pharmaceutically acceptable rate.

In addition to the foregoing advantages, the inorganic nature of the particles prepared according to the above-described process addresses the tendency of drug misusers to crush pharmaceuticals in an attempt to release the active ingredient contained therein. The relative hardness of the particles prepared according to the above-described process means that they are difficult, if not impossible, to crush using standard mortar and pestle.

In an embodiment, the at least one active ingredient is added at a quantity designed for extended release. More suitably, the at least one active ingredient is an opioid, opium derivative, or an opiate drug, including their isomers, esters, ethers and any salts thereof. More suitably, the at least one active ingredient is a drug defined as a "controlled substance" in the USA Controlled Substance Act, the Single Convention on Narcotic Drugs 1961 or the Misuse of Drugs Act 1971.

In another embodiment, the active ingredient comprises one or more of oxycodone, hydrocodone, oxymorphone, morphine, hydromorphone, dihydrocodeine, naloxone, or codeine, or a pharmaceutically acceptable salt thereof. Most suitably, the active ingredient is oxycodone, or a pharmaceutically acceptable salt thereof. Ethanol dose-dumping is an issue for almost all extended release medicaments, whose high dosages present an attractive target for drug misusers. Although opioid painkillers, in particular oxycodone, are incredibly potent analgesics, they can also lead to devastating addictions, thereby underlining the importance of the tamper-proof particles disclosed herein.

The term "opioid derivative" used herein will be understood to mean any known compound which acts as an opioid receptor agonist resulting in a therapeutically useful analgesic effect and is an alkaloid containing a pentacyclic core motif, and any acceptable pharmaceutical salts thereof.

In another embodiment, the at least one active ingredient may further comprise a non-opioid drug, such as a stimulant (e.g. pseudoephedrine). Alternatively, the opioid or opioid derivative may be the only active ingredient present within the pores of the particles.

In an embodiment, the percentage release of the active ingredient from the pores of the particles when 200 mg of the particles are placed in 900 mL of simulated intestinal fluid for 2 hours under stirring at 100 rpm is greater than or equal to the percentage release of the active ingredient from the pores of the particles when 200 mg of the particles are placed in 900 mL of 40% vol/vol ethanol in 0.1 M HCl for 2 hours under stirring at 100 rpm. Although the release properties of the particles have been expressed with respect to 40% vol/vol ethanol in 0.1 M HCl, it should be noted that the particles of the invention would be equally expected to exhibit beneficial release characteristics at other concentrations of ethanol (ranging from 5-100% vol/vol), or in other solvents (e.g. acetone).

Suitably the simulated intestinal fluid is pH 6.8 aqueous phosphate buffer at 37° C.±0.5° C., and the 40% vol/vol ethanol in 0.1 M HCl is at 37° C.±0.5° C. The above-outlined test conditions represent the standard conditions specified by the United States Pharmacopoeia (Chapter 711). In case of discrepancy between the above-outlined test conditions and the standard conditions defined by the United States Pharmacopoeia, the standard conditions shall prevail.

In another embodiment, the percentage release of the active ingredient into 40% vol/vol ethanol in 0.1 M HCl after 2 hours is less than or equal to 75%. Suitably, the percentage release of the active ingredient into 40% vol/vol ethanol in 0.1 M HCl after 2 hours is less than or equal to 70%. More suitably, the percentage release of the active ingredient into 40% vol/vol ethanol in 0.1 M HCl after 2 hours is less than or equal to 65%. Even more suitably, the percentage release of the active ingredient into 40% vol/vol ethanol in 0.1 M HCl after 2 hours is less than or equal to 60%. Even more suitably, the percentage release of the active ingredient into 40% vol/vol ethanol in 0.1 M HCl after 2 hours is less than or equal to 55%. Even more suitably, the percentage release of the active ingredient into 40% vol/vol ethanol in 0.1 M HCl after 2 hours is less than or equal to 50%. Most suitably, the percentage release of the active ingredient into 40% vol/vol ethanol in 0.1 M HCl after 2 hours is less than or equal to 45%.

In another embodiment, the percentage release of the active ingredient into the simulated intestinal fluid after 2 hours is less than or equal to 75%. The particles prepared according to the present method exhibit gradual (rather than immediate) release of the encapsulated active ingredient under physiological conditions, at a pharmaceutically acceptable rate. Suitably, the percentage release of the active ingredient into the simulated intestinal fluid after 2 hours is less than or equal to 70%. Most suitably, the percentage release of the active ingredient into the simulated intestinal fluid after 2 hours is less than or equal to 67.5%.

In another embodiment, in addition to the addition of the at least one active ingredient, step c) also comprises adding to the mixture of step b) one or more other compounds, such as, for example, pharmaceutically-acceptable excipients. The one or more other compounds may be added before, after or at the same time as the at least one active ingredients are added to the mixture of step b).

In another embodiment, step c) comprises adding to the mixture of step b) two or more active ingredients, and optionally one or more other compounds, such as, for example, pharmaceutically-acceptable excipients.

In another embodiment, the quantity of the at least one active ingredient added in step c) is 0-12.3 wt % based on the weight of the inorganic porous particle monomer. Suitably, the quantity of the at least one active ingredient added in step c) is 1.5-9.6 wt % based on the weight of the inorganic porous particle monomer. More suitably, the quantity of the at least one active ingredient added in step c) is 5.1-9.6 wt % based on the weight of the inorganic porous particle monomer. Even more suitably, the quantity of the at least one active ingredient added in step c) is 5.5-7.2 wt % based on the weight of the inorganic porous particle monomer.

In another embodiment, step a) comprises providing a mixture comprising water and HCl, said mixture having a pH in the range of 0.25-2.5. Suitably, step a) comprises providing a mixture comprising water and HCl, said mixture having a pH in the range of 0.25-2.25. More suitably, step a) comprises providing a mixture comprising water and HCl, said mixture having a pH in the range of 0.4-2.0. More suitably, step a) comprises providing a mixture comprising water and HCl, said mixture having a pH in the range of 0.4-1.25. Most suitably, step a) comprises providing a mixture comprising water and HCl, said mixture having a pH in the range of 0.4-0.6. In an embodiment, step a) comprises providing a mixture comprising water and HCl, said mixture having a pH of approximately 0.5 or 2. In a particular embodiment, step a) comprises providing a mixture comprising water and HCl, said mixture having a pH of approximately 2.

In another embodiment, step b) comprises adding to the mixture of step a) an inorganic porous particle monomer such that the molar ratio of water to the inorganic porous particle monomer ranges from 4.0-12.5. Suitably, step b) comprises adding to the mixture of step a) an inorganic porous particle monomer such that the molar ratio of water to the inorganic porous particle monomer ranges from 5.5-12. More suitably, step b) comprises adding to the mixture of step a) an inorganic porous particle monomer such that the molar ratio of water to the inorganic porous particle monomer ranges from 5.5-6.5. In an embodiment, step b) comprises adding to the mixture of step a) an inorganic porous particle monomer such that the molar ratio of water to the inorganic porous particle monomer is approximately 6 or 12. In a particular embodiment, step b) comprises adding to the mixture of step a) an inorganic porous particle monomer such that the molar ratio of water to the inorganic porous particle monomer is approximately 6.

It will be understood that the term "porous particle monomer" denotes an inorganic monomeric compound that is capable of reacting with itself under appropriate conditions to form an inorganic polymer. In an embodiment, the porous particle monomer is at least one alkoxysilane. Suitably, the porous particle monomer is at least one alkoxysilane selected from tetraethylorthosilicate (TEOS), tetramethoxysilane (TMOS), triethoxy-monoethylsilane (TrEES), triethoxy-mono-n-butylsilaneTrEnBS) and triethoxy-mono-t-butylsilane (TrEtBS). Most suitably, the porous particle monomer is tetraethylorthosilicate, having the following structure:

As discussed hereinbefore, from the standpoint of hardness, the inorganic nature of the particles prepared according to the process of the invention makes them highly resistant to crushing using standard kitchenware (e.g. pestle and mortar).

In another embodiment, either or both of drying steps d) and f) are performed at a temperature of 60-90° C. Suitably, either or both of steps d) and f) are performed at a temperature of 60-85° C. More suitably, either or both of steps d) and f) are performed at a temperature of 70-85° C.

In a particular embodiment, either or both of steps d) and f) are performed at a temperature of 75-85° C.

In another embodiment, either or both of steps d) and f) are performed for at least 24 hours. Suitably, step d) is performed for at least 72 hours. Suitably, step f) comprises drying the resulting porous particles such they have a moisture content of less than or equal to 1% by weight.

In a particular embodiment, both steps d) and f) are performed at a temperature of 75-85° C., step d) is performed for at least 72 hours, and step f) comprises drying the resulting porous particles such they have a moisture content of less than or equal to 1% by weight.

In another embodiment, step e) comprises milling the material resulting from step d) to a particle size of 150-350 µm. Suitably, step e) comprises milling the material resulting from step d) to a particle size of 185-350 µm. More suitably, step e) comprises milling the material resulting from step d) to a particle size of 300-330 µm.

It will be understood that particle sizes quoted herein refer to the range of particles present with diameters in the specified ranges following fractionation using test sieves. The specific size distribution of these particle populations is then also determined using a laser diffraction technique. Typically the d50, as determined by laser diffraction, is within ±10% of the midpoint of the targeted size range by sieve fractionation. As a consequence of the sieving process, the fractionated particle population usually contains a proportion of particles outside the targeted particle diameter range as seen in the particle size distribution established by laser diffraction.

In another embodiment, step e) comprises milling the material resulting from step d) to a particle size of 50-400 µm. Suitably, step e) comprises milling the material resulting from step d) to a particle size of 50-350 µm.

Alternatively, step e) comprises milling the material resulting from step d) to a particle size of 100-400 µm.

The process of the invention is a sol-gel process. Sol-gel processes involve the production of solid materials from small starting monomers by conversion of the monomers into a colloidal solution (sol) that acts as the precursor for an integrated network (gel) of either discrete particles or network polymers. Having regard to the present process, step c) can be conducted at any point during the sol-gel process, such that the at least one active ingredient may be added immediately after step b) is performed (in which case the mixture of step b) is still a free flowing solution), or the at least one active ingredient may be added once the solution has begun to gel. In an embodiment, the mixture of step b) is stirred for a period of 0-22 hours prior to the addition of the at least one active ingredient in step c). Suitably, the mixture of step b) is stirred for a period of 2-20 hours prior to the addition of the at least one active ingredient in step c). In another embodiment, the maximum viscosity at room temperature of the mixture of step b) prior to the addition of the at least one active ingredient in step c) is 2.0 Pa·s. Suitably, the maximum viscosity at room temperature of the mixture of step b) prior to the addition of the at least one active ingredient in step c) is 0.4 Pa·s. More suitably, the viscosity at room temperature of the mixture of step b) prior to the addition of the at least one active ingredient in step c) is approximately 0.3 Pa·s.

In a particular embodiment, the mixture of step b) is stirred for a period of 16-20 hours prior to the addition of the at least one active ingredient in step c). Suitably, the mixture of step b) is stirred for a period of approximately 18 hours prior to the addition of the at least one active ingredient in step c).

In another embodiment, the at least one active ingredient is added to the mixture of step b) when the temperature of the mixture is 17-26° C.

Particles of the Invention

As described hereinbefore, the present invention provides a plurality of particles obtained, directly obtained, or obtainable by a process described herein.

As described hereinbefore, the present invention also provides a particle comprising a porous substrate and at least one active ingredient present within the pores, wherein the at least one active ingredient is an opioid or opioid derivative and the particle has a particle size of 25-500 µm and a moisture content of less than or equal to 6% by weight, and wherein i. the percentage release of the at least one active ingredient from the particle in an aqueous solution of pH 6.8 at 37° C. is 30-50 after 1 hour, 45-65 after 2 hours, 60-80 after 4 hours and 85 or more after 10 hours, and ii. the percentage release of the at least one active ingredient from the particle in a solution of 40% vol/vol ethanol in 0.1 M HCl at 37° C. is 40 or less after 30 minutes, 50 or less after 1 hour and 65 or less after 2 hours.

The retarded release rate of the encapsulated active ingredient in alcoholic media when compared with that under physiological conditions makes the porous particles of the invention attractive from a drug delivery standpoint. Moreover, the particles of the invention release their payload gradually (rather than immediately) under physiological conditions, at a pharmaceutically acceptable rate. Furthermore, from the standpoint of hardness, the inorganic nature of the particles of the invention renders them highly resistant to drug misuse techniques that involve crushing pharmaceuticals with standard kitchenware equipment (e.g. pestle and mortar).

Release measurements quoted herein were obtained under standard conditions, as specified by the United States Pharmacopoiea (USP) guidelines, using a Distek USP I apparatus (basket dissolution tester). 900 mL of dissolution media (pH 6.8 phosphate buffer or 40% EtOH/0.1 M HCl) is first de-gassed and then equilibrated to 37° C.±0.5° C. 200 mg of the particles are then added to 150 mesh baskets and submerged into the dissolution media and stirred at 100 rpm. At the necessary time points, 9 mL of dissolution media was removed using a Distek autosampler and analysed for active ingredient content by UV/Vis spectroscopy.

It will be understood that the moisture content quoted herein in relation to the finished particles denote the moisture content when the particle has reached an equilibrated state in an air atmosphere at room temperature.

It will also be understood that the percentage release values quoted herein relates to the mass of the active ingredient released relative to the mass of the active ingredient contained within the particle prior to contacting the particle with the aqueous or alcoholic solution.

It will also be understood that terms such as "after 1 hour" and "after 2 hours" used herein indicate an exact period of time. Hence, the term "after 1 hour" refers to a measurement being taken after exactly 1 hour has elapsed.

In an embodiment, the percentage release of the at least one active ingredient from the particle in a solution of 40% ethanol in 0.1 M HCl at 37° C. is 25 or less after 30 minutes, 30 or less after 1 hour and 45 or less after 2 hours. Suitably, the percentage release of the at least one active ingredient from the particle in a solution of 40% ethanol in 0.1 M HCl at 37° C. is 20 or less after 30 minutes, 25 or less after 1 hour and 35 or less after 2 hours.

In another embodiment, the particles have a moisture content of less than or equal to 5% by weight.

In another embodiment, the particles have an average particle size of 125-375 µm. Suitably, the particles have an average particle size of 150-350 µm. More suitably, the particles have an average particle size of 185-350 µm. Most suitably, the particles have an average particle size of 300-330 µm.

In another embodiment, the particles have an average particle size of 50-400 μm. Suitably, the particles have an average particle size of 50-350 μm.

Alternatively, the particles have an average particle size of 100-400 μm.

Applications

As described hereinbefore, the present invention also provides tamper-proof, or abuse-deterrent, particles comprising a plurality of particles as defined herein.

The tamper-proof or abuse-deterrent particles of the present invention present an effective means of reducing, or even eliminating, the viability of dose-dumping drug misuse techniques. The particles prevent a user from achieving a rapid extraction of an active ingredient, either in vitro (i.e. intentionally), or in vivo (i.e. accidentally), thereby reducing the risk of users developing health issues linked to side effects, dependencies, or reduced efficacy of drugs. The surprising and advantageous characteristics of the particles in aqueous media mean that the efficacy of the tamper-proof, or abuse-deterrent, particles under physiological conditions is not compromised.

In another embodiment, the tamper-proof/abuse-deterrent particles are provided as a solid dosage form.

As described hereinbefore, the present invention also provides a solid dosage form comprising a particle defined herein.

In one embodiment, the solid dosage form is intended for oral or sublingual administration.

In another embodiment, the solid dosage form comprises a particle defined herein, wherein the particle comprises two or more pharmaceutically active compounds.

In another embodiment, the solid dosage form is an extended release dosage. Given that extended release dosages often contain high quantities of active ingredients, they pose an attractive target for drug misusers.

The solid dosage form comprises at least one opioid or opioid derivative active ingredient. Although opioids are widely used for their analgesic benefits, they are increasingly targeted by drug misusers. Suitably, the opioid is oxycodone or a pharmaceutically acceptable salt thereof.

In another embodiment, the solid dosage form is suitable for use as, or alongside, an abuse-deterrent medicament.

EXAMPLES

Examples of the invention will now be described, for the purpose of reference and illustration only, with reference to the accompanying figures, in which.

Preparation of Particles

Deionised water and hydrochloric acid were mixed to achieve the starting pH values shown in Table 1. Tetraethoxyorthosilane (TEOS) (3.50 kg, 16.80 moles) was then added. The reaction beaker was covered and left to stir at room temperature. Oxycodone hydrochloride (252 g, 717.80 mmoles) was subsequently added to the reaction mixture at the appropriate time point indicated in Table 1. After 18 hours the beaker covering was removed and the reaction left to stir at room temperature until gelling occurred. Portions of the wet gel were placed in an oven at 60 or 80° C. for a minimum of 24 hours. The resulting sol-gel glass chunks were then milled to the desired product particle size range. The milled powders were then put back in the oven at 60 or 80° C. until the moisture content of the samples had reached a minimum value.

Table 1 shown below provides processing parameters and characterisation data for Examples 1-5, as well as for Comparators C1-C4.

TABLE 1

Preparation variables for desirable uncoated formulations

| Entry | Water:TEOS molar ratio | pH | Drying temp (° C.) | Drug addition (hours) | Particle size range (μm) | $D_{50}$ (μm) | Loss on drying at 105° C. (%) |
|---|---|---|---|---|---|---|---|
| 1 | 12 | 2 | 60 | 9 | 150-250 | 206 | 1.91 |
| 2 | 12 | 2 | 60 | 9 | 150-250 | 193 | 1.32 |

TABLE 1-continued

Preparation variables for desirable uncoated formulations

| Entry | Water:TEOS molar ratio | pH | Drying temp (° C.) | Drug addition (hours) | Particle size range (μm) | $D_{50}$ (μm) | Loss on drying at 105° C. (%) |
|---|---|---|---|---|---|---|---|
| 3 | 6 | 0.5 | 80 | 18 | 250-350 | 328 | 0.83 |
| 4 | 6 | 0.5 | 80 | 3 | 250-350 | 319 | 1.75 |
| 5 | 6 | 0.5 | 80 | 15 | 250-350 | 333 | 0.82 |
| C1 | 18 | 0.5 | 80 | 0 | 250-350 | 295 | 1.42 |
| C2 | 18 | 0.5 | 80 | 18 | 50-150 | 96 | 1.97 |
| C3 | 6 | 3.5 | 80 | 18 | 50-150 | 104 | 0.79 |
| C4 | 6 | 0.5 | 40 | 18 | 50-150 | 102 | 5.51 |

Particle size ranges were achieved by sieving the milled sol-gel particles using appropriate combinations of 53, 150, 250 and 355 μm sieves. The particle size range for each formulation was then analysed for its particle size distribution using a Malvern Mastersizer 2000 fitted with a dry-state laser diffraction analyser Release Studies Standard conditions as specified by the United States Pharmacopoiea (USP) guidelines were followed, using a Distek USP I apparatus (basket dissolution tester).

900 mL of dissolution media (pH 6.8 phosphate buffer or 40% EtOH/0.1 M HCl) was first de-gassed and then equilibrated to 37° C.±0.5° C. 200 mg of the formulation with the desired particle size distribution was added to 150 mesh baskets and submerged into the dissolution media and stirred at 100 rpm. At the necessary time points (30, 60 and 120 minutes for EtOH/HCl media and 1, 2, 4, 6, 8 and 10 hours for phosphate buffer) 9 mL of dissolution media was removed using a Distek autosampler and analysed for oxycodone content by UV/Vis spectroscopy. All release studies were repeated in triplicate.

The results are provided in Table 2 below, and in FIGS. 1-9.

Figure 1:
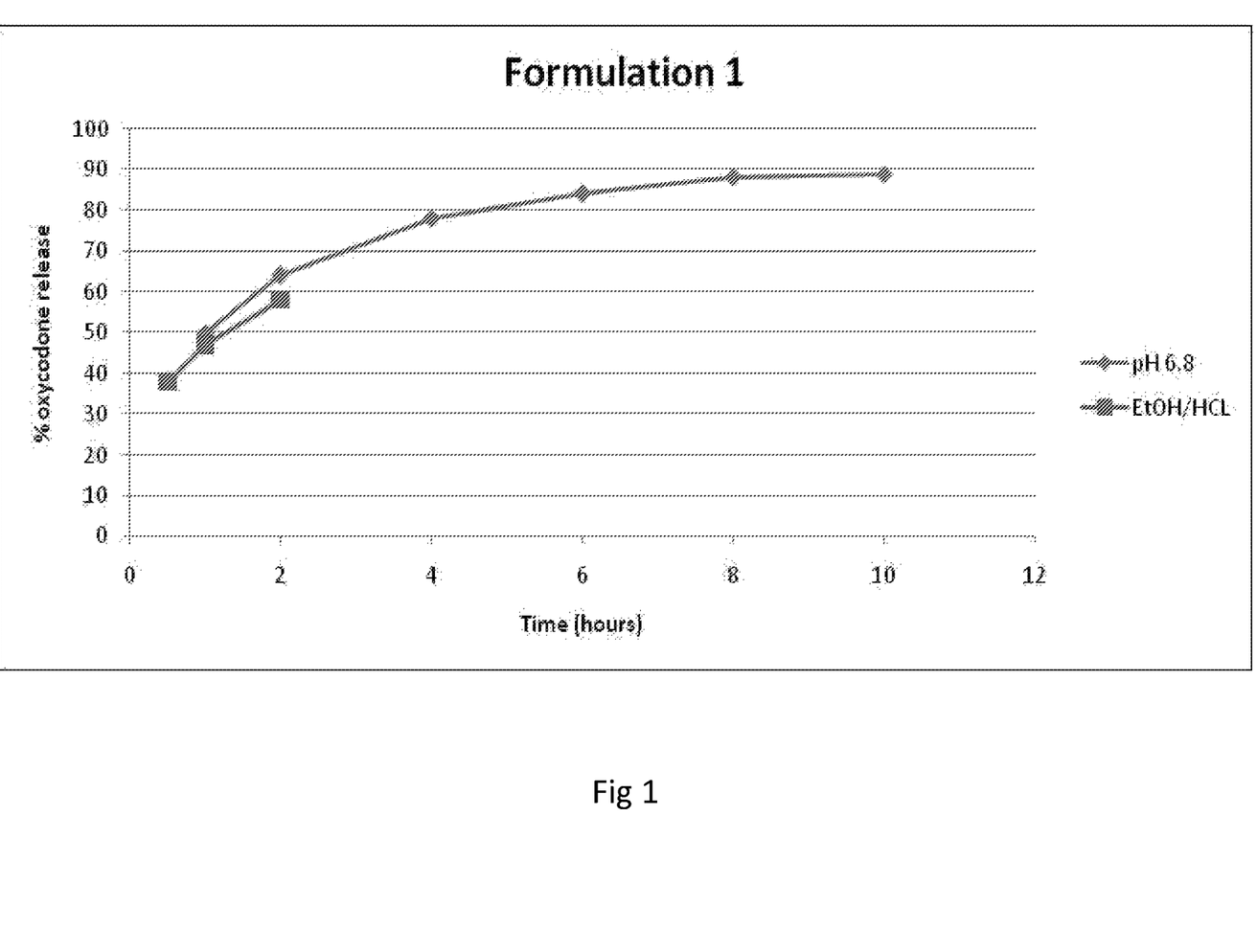
FIG. 1 shows percentage release of oxycodone HCl from Example 1 particles in a) pH 6.8 aqueous buffer solution (diamond symbol), and b) 40% ethanol/HCl solution (square symbol).
Figure 2:
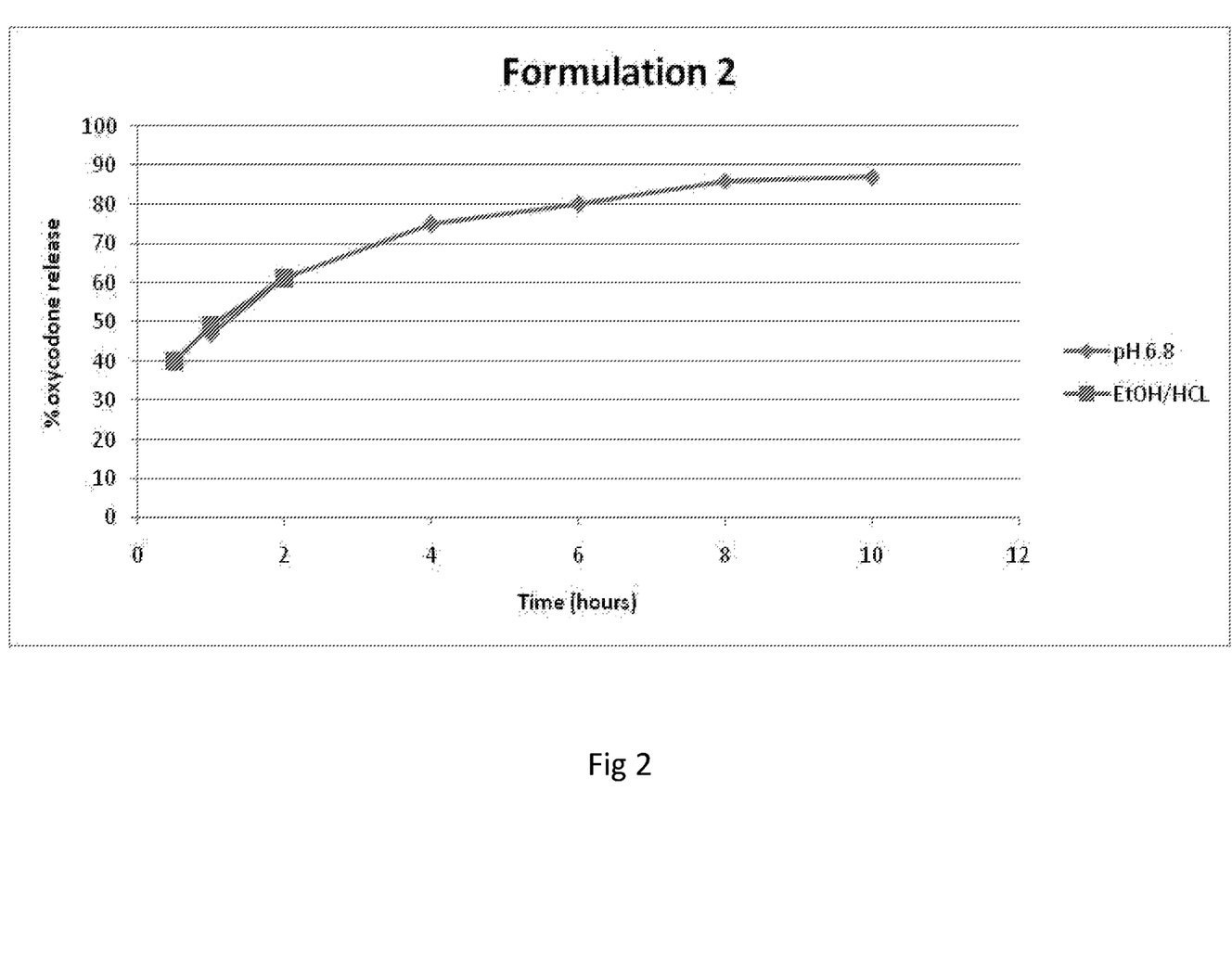
FIG. 2 shows percentage release of oxycodone HCl from Example 2 particles in a) pH 6.8 aqueous buffer solution (diamond symbol), and b) 40% ethanol/HCl solution (square symbol).
Figure 3:
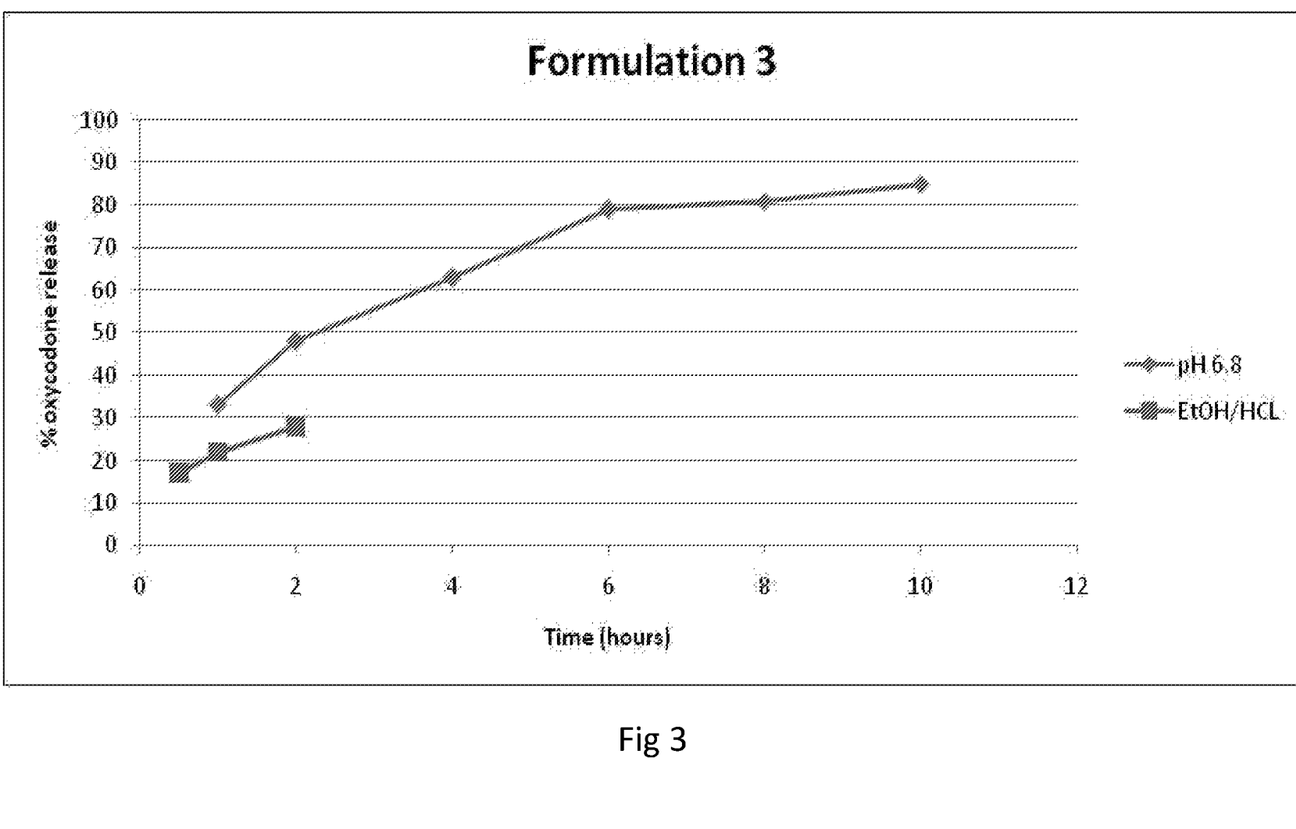
FIG. 3 shows percentage release of oxycodone HCl from Example 3 particles in a) pH 6.8 aqueous buffer solution (diamond symbol), and b) 40% ethanol/HCl solution (square symbol).
Figure 4:
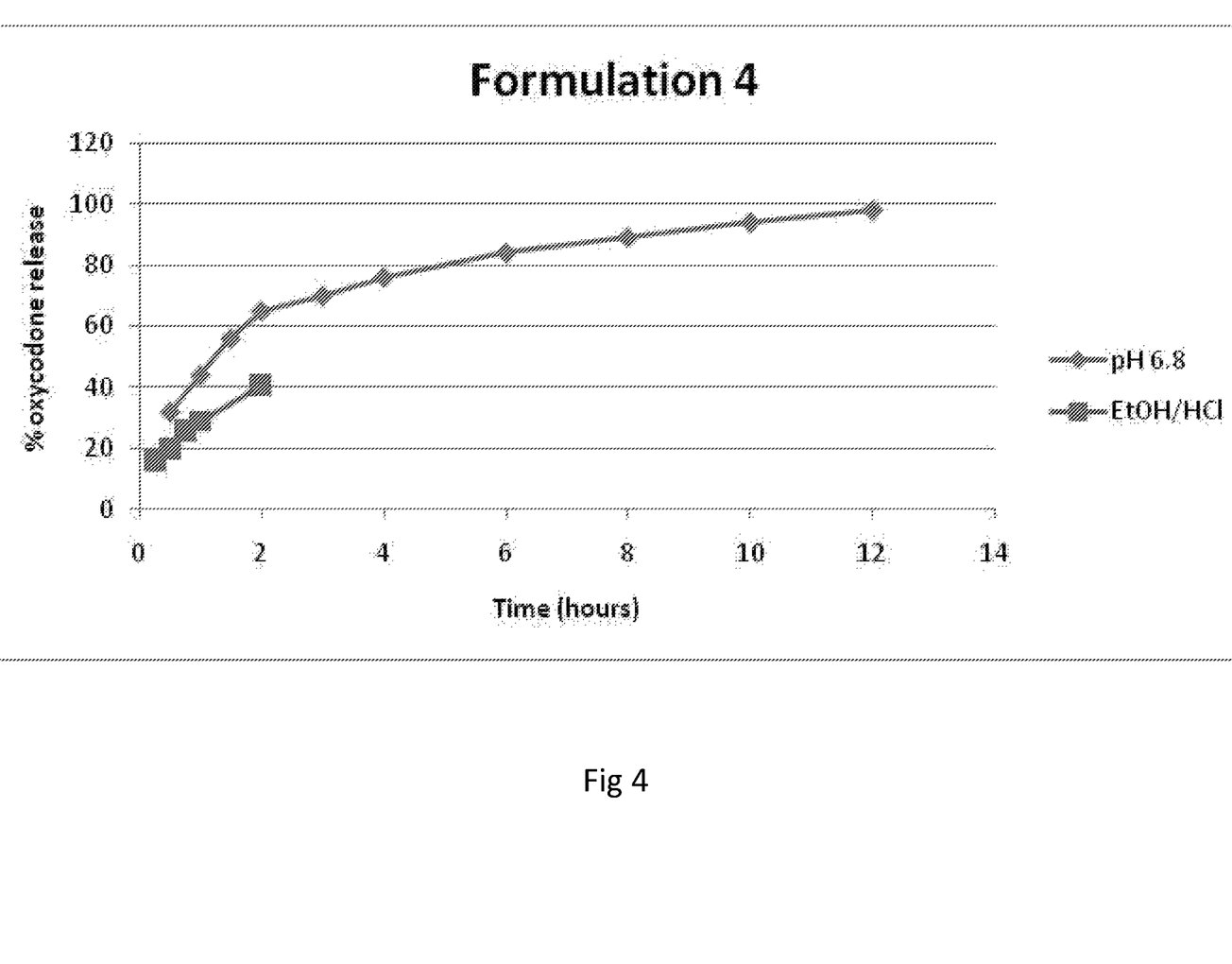
FIG. 4 shows percentage release of oxycodone HCl from Example 4 particles in a) pH 6.8 aqueous buffer solution (diamond symbol), and b) 40% ethanol/HCl solution (square symbol).
Figure 5:
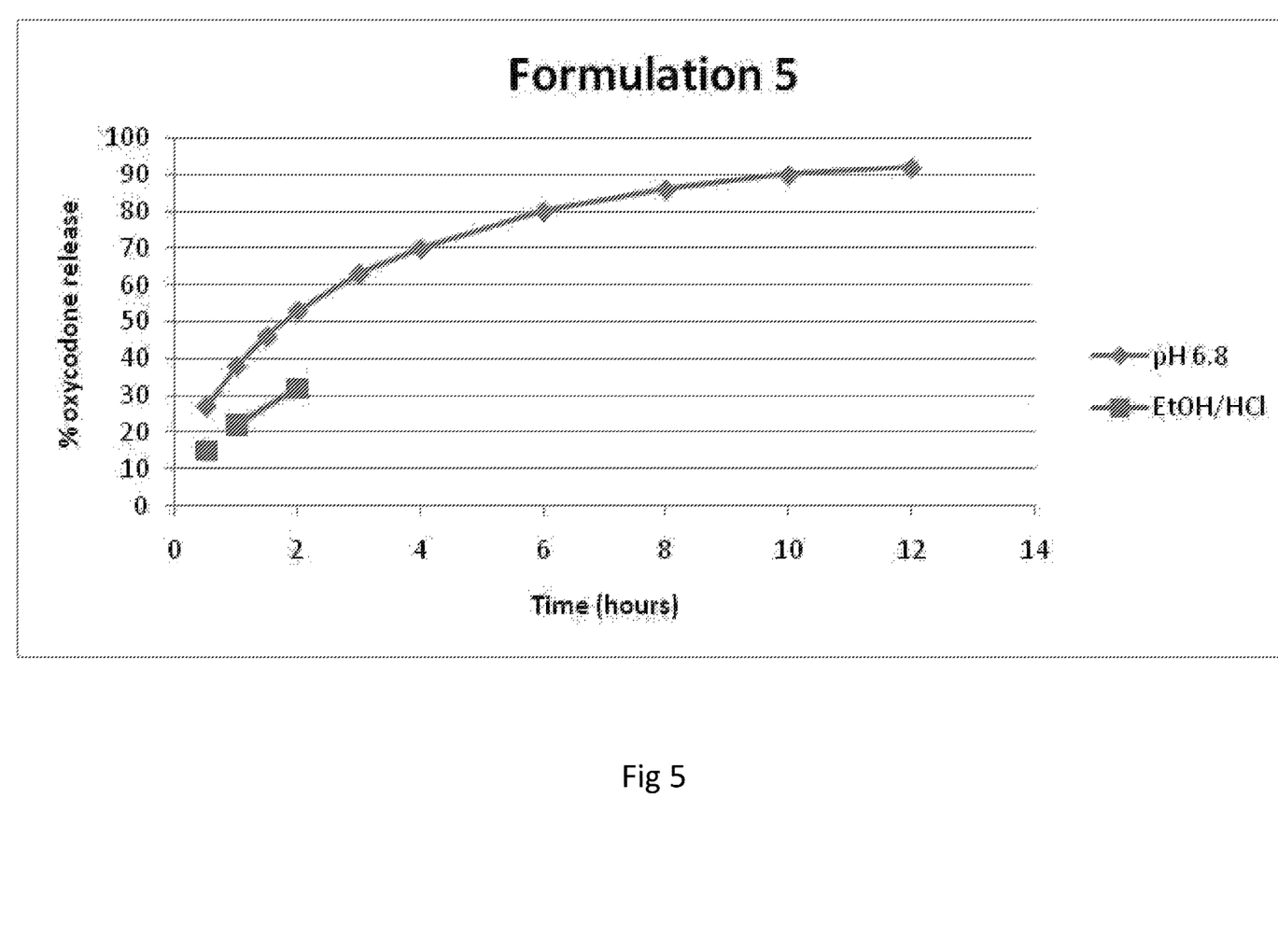
FIG. 5 shows percentage release of oxycodone HCl from Example 5 particles in pH 6.8 aqueous buffer solution (diamond symbol), and b) 40% ethanol/HCl solution (square symbol).
Figure 6:
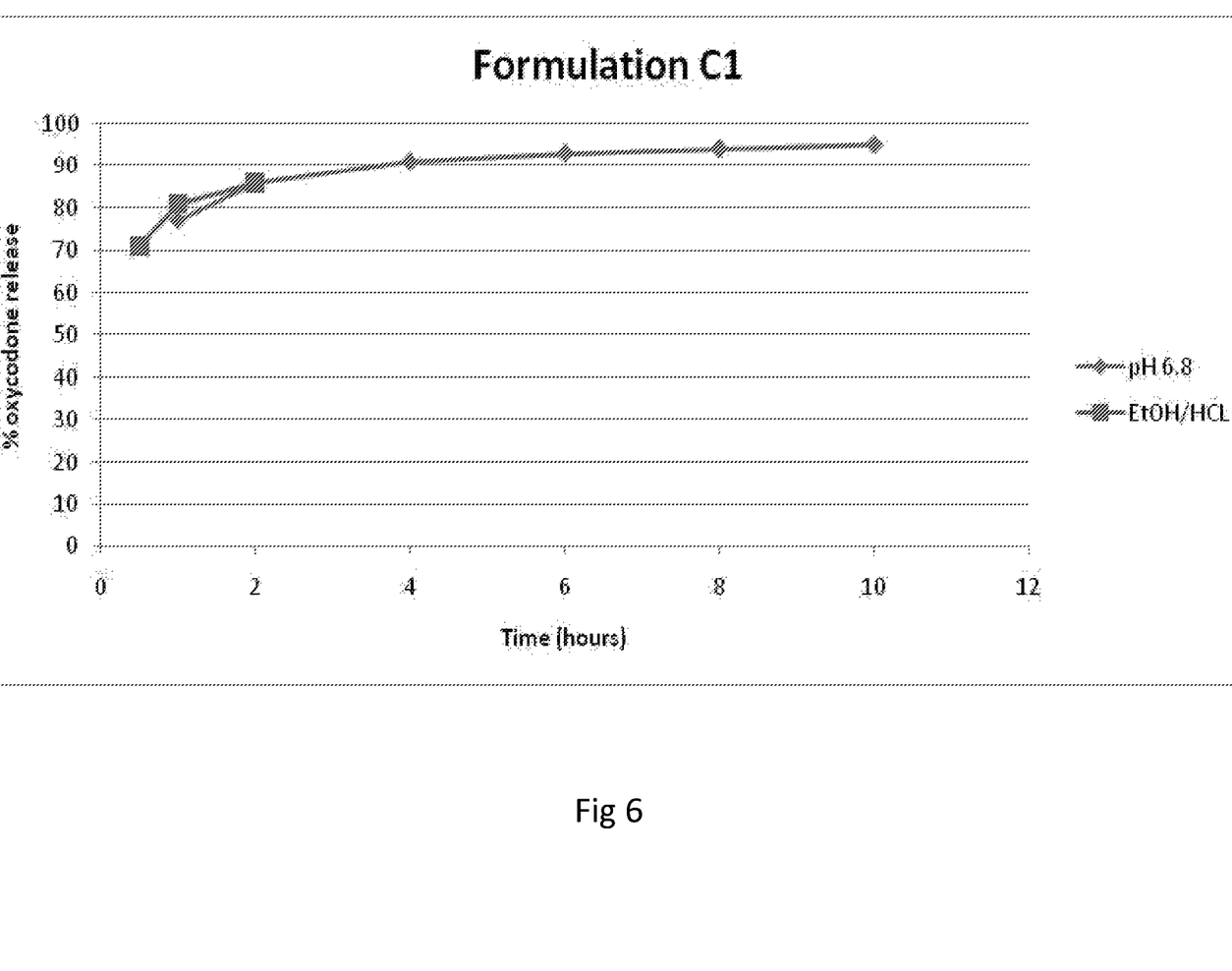
FIG. 6 shows percentage release of oxycodone HCl from Comparator C1 particles in a) pH 6.8 aqueous buffer solution (diamond symbol), and b) 40% ethanol/HCl solution (square symbol).
Figure 7:
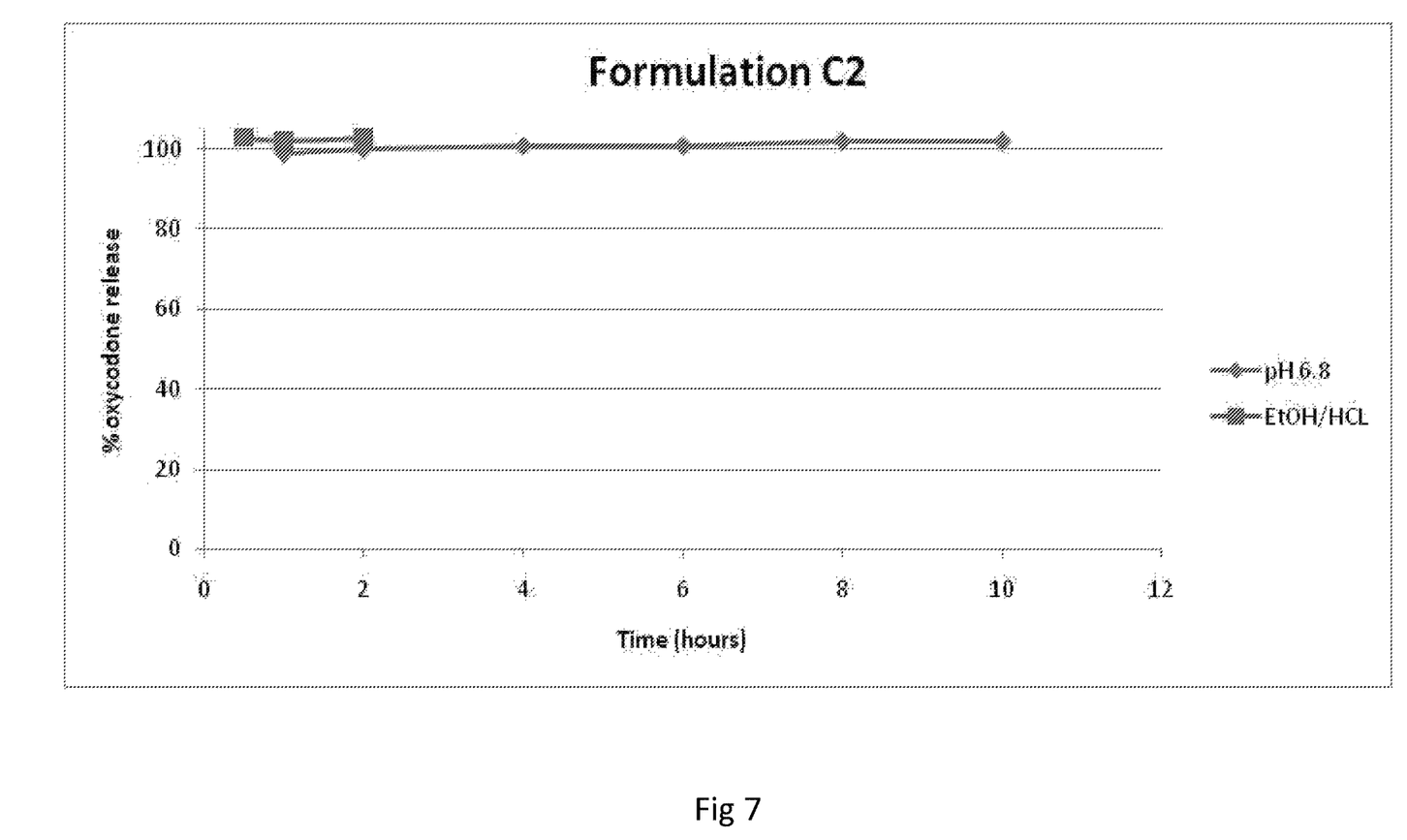
FIG. 7 shows percentage release of oxycodone HCl from Comparator C2 particles in a) pH 6.8 aqueous buffer solution (diamond symbol), and b) 40% ethanol/HCl solution (square symbol).
Figure 8:
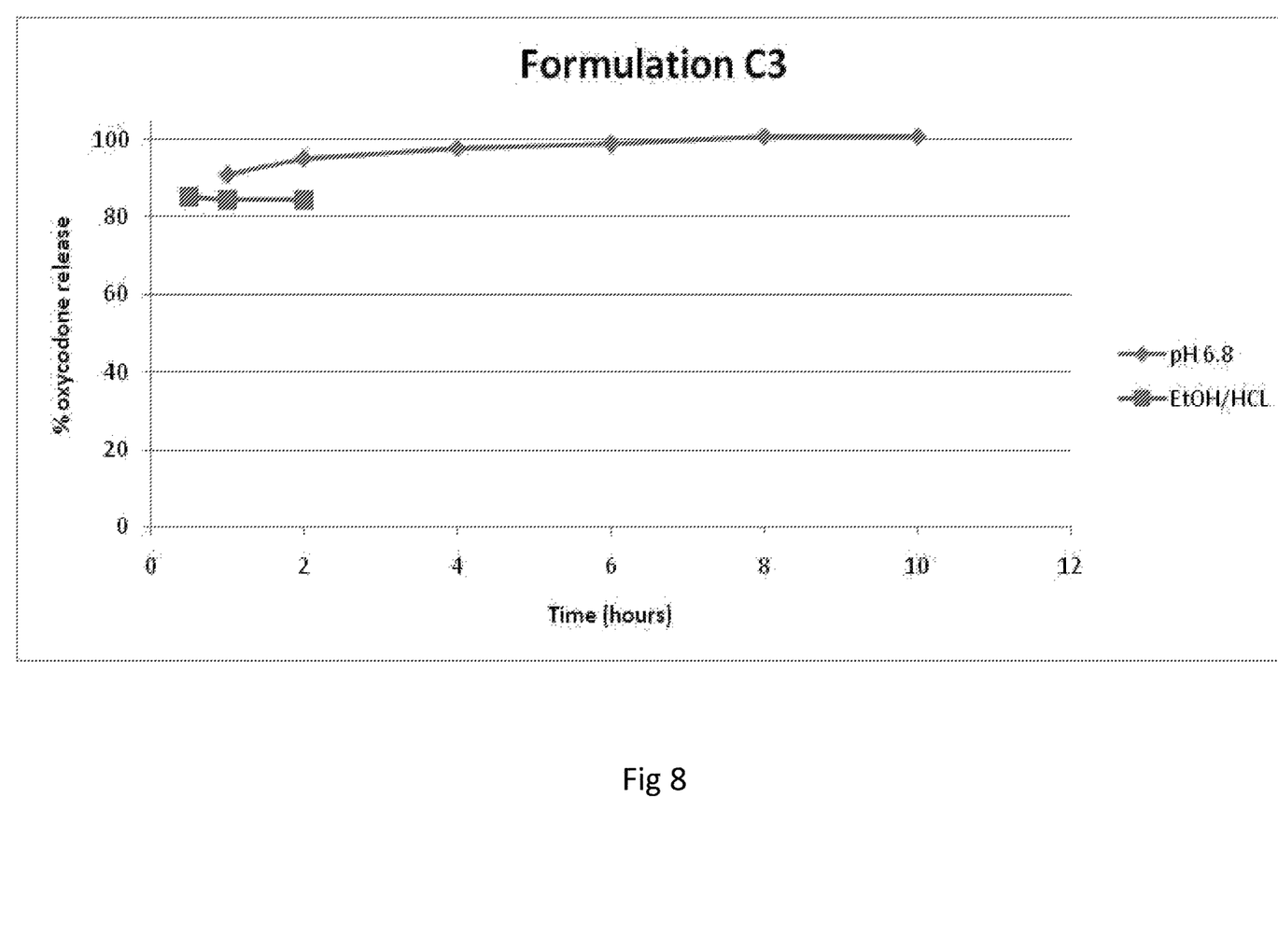
FIG. 8 shows percentage release of oxycodone HCl from Comparator C3 particles in a) pH 6.8 aqueous buffer solution (diamond symbol), and b) 40% ethanol/HCl solution (square symbol).
Figure 9:
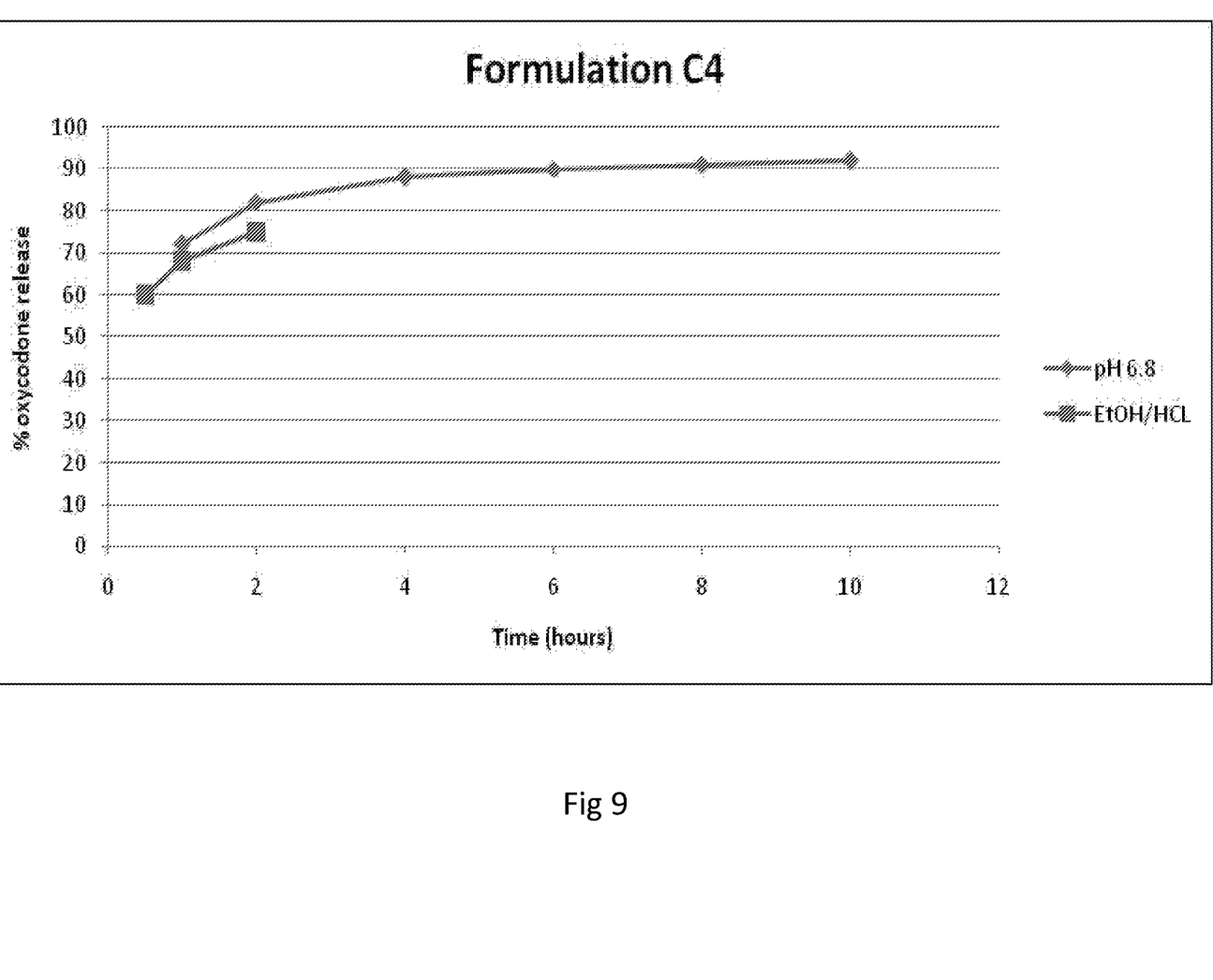
FIG. 9 shows percentage release of oxycodone HCl from Comparator C4 particles in a) pH 6.8 aqueous buffer solution (diamond symbol), and b) 40% ethanol/HCl solution (square symbol).
Figure 10:
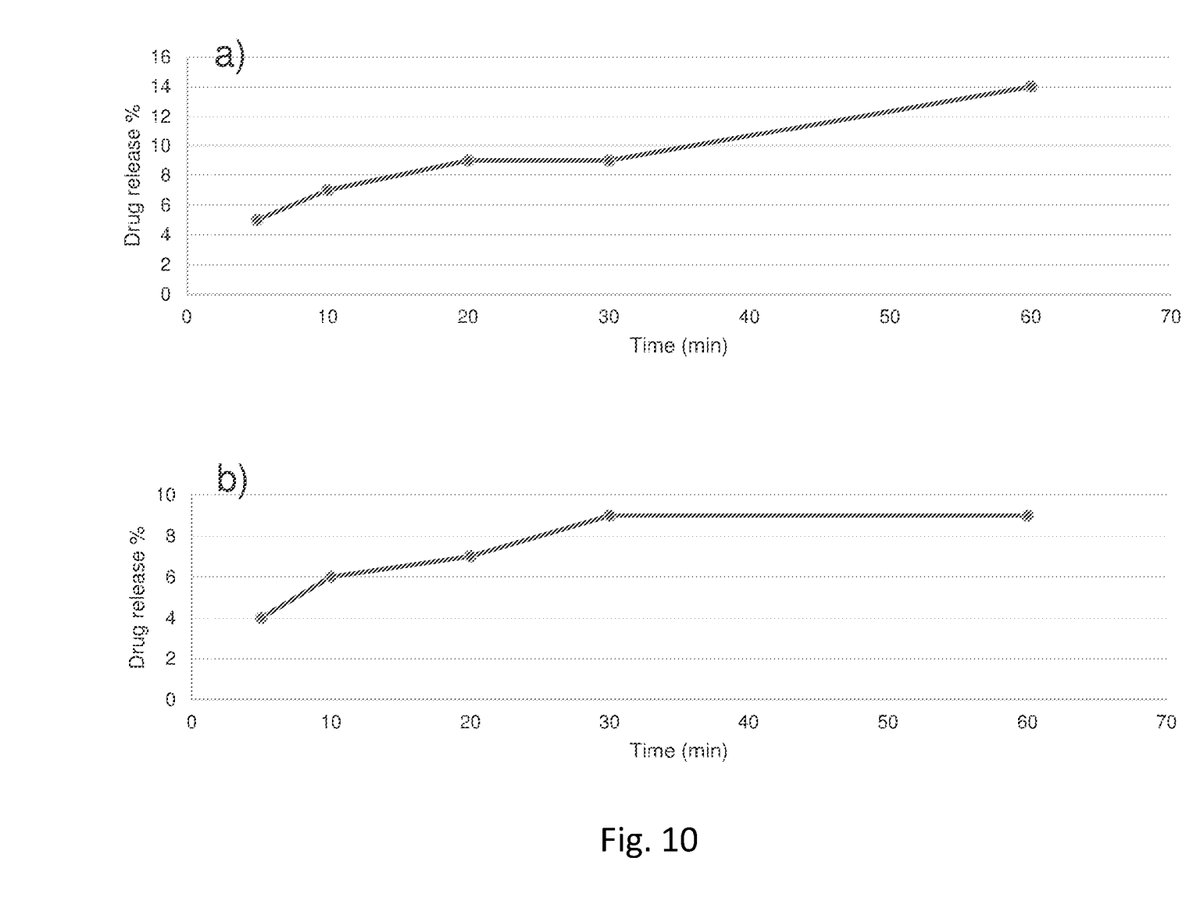
FIG. 10 shows a) percentage release of oxycodone HCl from Example 3 particles in neat ethanol; and b) percentage release of oxycodone HCl from Example 3 particles in neat acetone.

FIG. 10 compares the percentage release of oxycodone HCl from Formulation 3 into neat acetone and neat ethanol over the course of 60 minutes. The conditions of the experiment were identical to those used when investigating release into 40% vol/vol ethanol in 0.1 M HCl. The data show that release of the active ingredient is retarded to an even greater extent in neat ethanol and acetone.

While specific embodiments of the invention have been described herein for the purpose of reference and illustration, various modifications will be apparent to a person skilled in the art without departing from the scope of the invention as defined by the appended claims.

REFERENCES

1. National Institute on Drug Abuse (NIDA) NIDA Community Drug Alert Bulletin:
   Prescription Drugs. Bethesda, Md: U.S. Department of Health and Human Services; 2005. NIH Pub. No. 05-0580. Available at: http://archives.drugabuse.gov/prescripalert/. Accessed Nov. 1, 2011.
2. Passik S D, Kirsh K L, Donaghy K B, Portenoy R K. Pain and aberrant drug-related behaviors in medically ill patients with and without histories of substance abuse. Clin J Pain. 2006; 22(2):173-181.[PubMed]

TABLE 2

Release of oxycodone HCl in 40% EtOH/0.1M HCl and pH 6.8 phosphate buffer

| | % Oxycodone release at time point (hours) | | | | | | | | |
|---|---|---|---|---|---|---|---|---|---|
| | pH 6.8 phosphate buffer | | | | | | 40% EtOH/0.1M HCl | | |
| Entry | 1 | 2 | 4 | 6 | 8 | 10 | 0.5 | 1 | 2 |
| 1 | 50 | 64 | 78 | 84 | 88 | 89 | 38 | 47 | 58 |
| 2 | 47 | 61 | 75 | 80 | 86 | 87 | 40 | 49 | 61 |
| 3 | 33 | 48 | 63 | 79 | 81 | 85 | 17 | 22 | 28 |
| 4 | 44 | 65 | 76 | 84 | 89 | 94 | 20 | 29 | 41 |
| 5 | 38 | 53 | 70 | 80 | 86 | 90 | 15 | 22 | 32 |
| C1 | 77 | 86 | 91 | 93 | 94 | 95 | 71 | 81 | 86 |
| C2 | 99 | 100 | 101 | 101 | 102 | 102 | 103 | 102 | 103 |
| C3 | 91 | 95 | 98 | 99 | 101 | 101 | 85 | 84 | 84 |
| C4 | 72 | 82 | 88 | 90 | 91 | 92 | 60 | 68 | 75 |

It is clear from the data appearing in Table 2, and illustrated in FIGS. 1-9, that porous particles prepared according to the process of the invention (Examples 1-5) exhibit markedly improved release characteristics when compared with particles that have been otherwise prepared. Not only do Examples 1-5 demonstrate significant retardation of active ingredient release in alcoholic media, but they also show a gradual (as opposed to immediate) release of the active in aqueous phosphate buffer, which is in line with the values observed with the market leading product.

The invention claimed is:

1. A sol-gel process for the preparation of a plurality of porous particles comprising at least one active ingredient present within the pores, wherein the at least one active ingredient is an opioid or opioid derivative and wherein the percentage release of the active ingredient from the pores of the particles into simulated intestinal fluid is greater than or equal to the percentage release of the active ingredient from the pores of the particles into 40% vol/vol ethanol in 0.1 M HCl, the process comprising the steps of:
a) providing a mixture comprising water and HCl, said mixture having a pH of less than or equal to 2.5,
b) adding to the mixture of step a) an inorganic porous particle monomer such that the molar ratio of water to the inorganic porous particle monomer is less than or equal to 12.5,
c) adding to the mixture of step b) at least one active ingredient, wherein the at least one active ingredient comprises an opioid or opioid derivative,
d) drying the mixture resulting from step c) at a temperature of greater than or equal to 60°C.,
e) milling the material resulting from step d) to a particle size of 25-500 µm, and
f) drying the resulting porous particles at a temperature of greater than or equal to 60°C.;
wherein on addition of the at least one active ingredient to the mixture of step b), the mixture of step b) is a colloidal solution with a maximum viscosity at room temperature of 2.0 Pa·s; and drying steps d) and (f) are performed at a temperature of 60-90 °C.

2. The process of claim 1, wherein the at least one active ingredient comprises an opioid or opioid derivative selected from oxycodone, codeine, hydrocodone, dihydrocodeine, morphine, oxymorphone, hydromorphone, naloxone or a pharmaceutically acceptable salt thereof.

3. The process of claim 1, wherein the at least one active ingredient comprises an opioid or opioid derivative selected from oxycodone, oxymorphone, hydrocodone, morphine or a pharmaceutically acceptable salt thereof.

4. The process of claim 1, wherein the at least one active ingredient comprises oxycodone or a pharmaceutically acceptable salt thereof.

5. The process of claim 1, wherein the percentage release of the active ingredient from the pores of the particles when 200 mg of the particles are placed in 900 mL of simulated intestinal fluid for 2 hours under stirring at 100 rpm is greater than or equal to the percentage release of the active ingredient from the pores of the particles when 200 mg of the particles are placed in 900 mL of 40% vol/vol ethanol in 0.1 M HCl for 2hours under stirring at 100 rpm.

6. The process of claim 5, wherein the simulated intestinal fluid is pH 6.8 aqueous phosphate buffer at 37°C. ±0.5 °C., and the 40% vol/vol ethanol in 0.1 M HCl is at 37°C. ±0.5 °C.

7. The process of claim 5, wherein the percentage release of the active ingredient from the pores of the particles when 200 mg of the particles are placed in 900 mL of simulated intestinal fluid for 2 hours under stirring at 100 rpm is greater than the percentage release of the active ingredient from the pores of the particles when 200 mg of the particles are placed in 900 mL of 40% vol/vol ethanol in 0.1 M HCl for 2 hours under stirring at 100 rpm.

8. The process of claim 5, wherein the percentage release of the active ingredient into 40% vol/vol ethanol in 0.1 M HCl after 2 hours is less than or equal to 75%.

9. The process of claim 5, wherein the percentage release of the active ingredient into the simulated intestinal fluid after 2 hours is less than or equal to 70%.

10. The process of claim 1, wherein the quantity of the at least one active ingredient added in step c) is 0-12.3 wt % based on the weight of the inorganic porous particle monomer.

11. The process of claim 1, wherein step a) comprises providing a mixture comprising water and HCl, said mixture having a pH in the range of 0.25-2.25.

12. The process of claim 1, wherein step b) comprises adding to the mixture of step a) an inorganic porous particle monomer such that the molar ratio of water to the inorganic porous particle monomer ranges from 4.0-12.5.

13. The process of claim 1, wherein the inorganic porous particle monomer is a silane, capable of forming a silicate.

14. The process of claim 1, wherein step e) comprises milling the material resulting from step d) to a particle size of 50-400 µm.

15. The process of claim 1, wherein the viscosity of the mixture resulting from either or both of steps b) and c) increases prior to performing the next step.

16. A plurality of porous particles obtainable by the process according to claim 1.

17. The plurality of porous particles of claim 16, wherein the moisture content of the particles is less than or equal to 6% by weight.

18. A tamper-proof dosage form comprising the plurality of particles of claim 16.

19. A solid dosage form comprising the plurality of particles of claim 17.

20. A particle comprising a porous substrate and at least one active ingredient present within the pores, wherein the at least one active ingredient is an opioid or opioid derivative and the particle has a particle size of 25-500 µm and a moisture content of less than or equal to 6% by weight, and wherein
i. the percentage release of the at least one active ingredient from the particle in an aqueous solution of pH 6.8 at 37°C. is 30-50 after 1 hour, 45-65 after 2 hours, 60-80 after 4hours and 85 or more after 10 hours, and
ii. the percentage release of the at least one active ingredient from the particle in a solution of 40% vol/vol ethanol in 0.1 M HCl at 37°C. is 40 or less after 30 minutes, 50 or less after 1 hour and 65 or less after 2 hours.

* * * * *